(12) United States Patent
Lorant

(10) Patent No.: US 9,757,313 B2
(45) Date of Patent: Sep. 12, 2017

(54) COSMETIC OIL-IN-WATER EMULSION

(75) Inventor: Raluca Lorant, Thiais (FR)

(73) Assignee: L'OREAL, Paris (FR)

( * ) Notice: Subject to any disclaimer, the term of this patent is extended or adjusted under 35 U.S.C. 154(b) by 1233 days.

(21) Appl. No.: 12/212,253

(22) Filed: Sep. 17, 2008

(65) Prior Publication Data

US 2009/0105353 A1  Apr. 23, 2009

Related U.S. Application Data

(60) Provisional application No. 60/978,162, filed on Oct. 8, 2007.

(30) Foreign Application Priority Data

Sep. 24, 2007  (FR) ...................... 07 57800

(51) Int. Cl.
*A61K 8/06* (2006.01)
*A61K 8/42* (2006.01)
*A61K 8/81* (2006.01)
*A61Q 19/00* (2006.01)
*A61Q 17/04* (2006.01)
*A61K 8/49* (2006.01)

(52) U.S. Cl.
CPC .............. *A61K 8/06* (2013.01); *A61K 8/062* (2013.01); *A61K 8/4993* (2013.01); *A61K 8/8152* (2013.01); *A61Q 17/04* (2013.01); *A61Q 19/00* (2013.01); *A61K 2800/54* (2013.01)

(58) Field of Classification Search
CPC ........ A61K 8/062; A61K 8/8152; A61K 8/42; A61Q 17/04; A61Q 19/00
See application file for complete search history.

(56) References Cited

U.S. PATENT DOCUMENTS

| 5,156,911 | A |  | 10/1992 | Stewart |  |
| 5,519,063 | A | * | 5/1996 | Mondet et al. | 514/772.4 |
| 5,736,125 | A |  | 4/1998 | Morawsky et al. |  |
| 6,710,022 | B1 | * | 3/2004 | Kwetkat | A61K 8/04 510/119 |
| 6,989,417 | B2 | * | 1/2006 | Bitler et al. | 524/474 |
| 7,022,316 | B2 | * | 4/2006 | Galdi et al. | 424/59 |
| 2004/0005279 | A1 | * | 1/2004 | Lorant | A61K 8/042 424/60 |
| 2005/0031653 | A1 |  | 2/2005 | Kwetkat et al. |  |
| 2005/0063925 | A1 | * | 3/2005 | Candau et al. | 424/59 |
| 2009/0041691 | A1 | * | 2/2009 | Candau et al. | 424/60 |

FOREIGN PATENT DOCUMENTS

| EP | 0 951 897 A2 | 10/1999 |
| EP | 1 331 000 A1 | 7/2003 |
| EP | 1 502 582 A1 | 2/2005 |
| FR | 2 863 889 A1 | 6/2005 |
| WO | WO 01/19333 A1 | 3/2001 |
| WO | WO 03/024412 A2 | 3/2003 |
| WO | WO 2004/105704 | * 12/2004 |
| WO | WO 2004/105704 A2 | 12/2004 |
| WO | WO 2007/054824 A2 | 5/2007 |

OTHER PUBLICATIONS

Ceralution H (Sasol, EC-Safety Data Sheet, revised Nov. 29, 2007, p. 1-5).*
B. Boutevin, et al., "Study of Morphological and Mechanical Properties of PP/PBT Blends," Polymer Bulletin, vol. 34, pp. 117-123 (1995).
S. Nojima, et al., "Melting Behavior of Poly(ε-caprolactone)-block-Polybutadiene Copolymers," Macromolecules 1999, vol. 32, No. 11, pp. 3727-3734.
P. Rangarajan, et al., "Morphology of Semicrystalline Block Copolymers of Ethylene-(Ethylene-alt-propylene)," Macromolecules, 1993, vol. 26, No. 17, pp. 4640-4645.
D. Richter, et al., "Polymer Aggregates with Crystalline Cores: The System Polyethylene-Poly(ethylenepropylene)," Macromolecules 1997, vol. 30, No. 4, pp. 1053-1068.
I.W. Hamley, "Crystallization in Block Copolymers," Advances in Polymer Science, vol. 148, 1999, pp. 114-137.

* cited by examiner

*Primary Examiner* — Bethany Barham
*Assistant Examiner* — Peter Anthopolos
(74) *Attorney, Agent, or Firm* — Joel S. Armstrong

(57) ABSTRACT

A cosmetic or dermatological compositions of oil-in-water emulsion type, including, in a physiologically acceptable medium, at least gemini surfactant of formula (I):

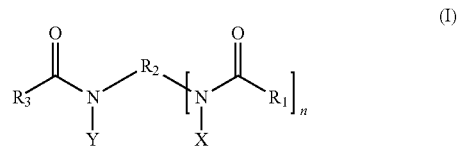

in which $R_1$ and $R_3$ denote, independently of one another, an alkyl radical containing from 1 to 25 carbon atoms; $R_2$ denotes a spacer consisting of a linear or branched alkylene chain containing from 1 to 12 carbon atoms; X and Y denote, independently of one another, a group $-(C_2H_4O)_a-(C_3H_6O)_b Z$; n ranges from 1 to 10, in combination with an effective amount of at least one semi-crystalline polymer which is solid at ambient temperature and which has a melting point below 70° C., said polymer having a number-average molecular mass greater than or equal to 2000, said emulsion having a proportion of fatty phase of greater than 10% by weight relative to the total weight of the composition and including more than 40% by weight of non-volatile oil(s) relative to the weight of the fatty phase.

15 Claims, No Drawings

COSMETIC OIL-IN-WATER EMULSION

This non provisional application claims the benefit of French Application No. 07 57800 filed on Sep. 24, 2007 and U.S. Provisional Application No. 60/978,162 filed on Oct. 8, 2007.

The present disclosure relates to the field of cosmetic compositions of emulsion type and more particularly to the field of compositions comprising a textured liquid fatty phase.

BACKGROUND

Cosmetic compositions comprising a liquid fatty phase are commonly used nowadays, in particular for cleansing, caring for, making up and/or treating the skin, the hair and the scalp. The daily use of these compositions means that those using them are always more demanding and more sensitive to the texture more generally to the organoleptic properties of these compositions.

Thus, it has been noted that cosmetic compositions which comprise more than 10% by weight of fatty phase containing more than 40% by weight of non-volatile oil, are found to be advantageous for making up for the lack of cutaneous lipids in dehydrated skin, but on the other hand can pose problems in terms of sensory properties, insofar as they are capable of generating a greasy effect, sometimes accompanied by a tacky effect and/or a shiny appearance, which users do not find attractive.

In addition to this undesirable effect from a sensory perception point of view, these emulsion-type compositions can show a lack of stability when they are combined with certain materials. Thus, it has been noted that the presence of large amounts of UV screens, in particular organic UV screens, in emulsions of this type can affect the stability thereof over time, or even initiate demixing thereof. The composition then becomes inhomogeneous and is no longer usable.

SUMMARY

There remains therefore, at this time, a need for emulsion-type cosmetic compositions with a significant fatty phase content, which are reproducible on demand in terms of viscosity, which are devoid of any fatty, tacky and shiny nature, and which have improved stability, in particular when they contain materials of organic UV screen type.

The principal object of the present disclosure is precisely to meet these needs.

In this regard, the inventors have, unexpectedly, noted that it is possible to obtain such emulsions, with the proviso of using therein, by way of emulsifier, a particular gemini surfactant in combination with at least one specific semi-crystalline polymer.

Document EP1 502 582 describes compositions comprising at least one gemini surfactant and at least one associative polymer, said compositions being fluid and emulsified and containing a photoprotective system capable of screening UV rays.

Documents WO 2007/054824, WO 03/024412 and WO 2004/105704 describes moreover, oil-in-water compositions for topical application, comprising at least one gemini surfactant.

Furthermore, documents FR 2 863 889 and EP 1 331 000 describe compositions which use semi-crystalline polymers.

However, none of there documents either describes or suggests the use of the combination of the disclosure in the galenical architecture more particularly targeted, namely comprising more than 10% by weight of fatty phase containing more than 40% by weight of non-volatile oil.

DETAILED DESCRIPTION OF EMBODIMENTS

More specifically, a subject of the disclosure is a cosmetic or dermatological composition of oil-in-water type comprising, in a physiologically acceptable medium, at least one gemini surfactant of formula (I):

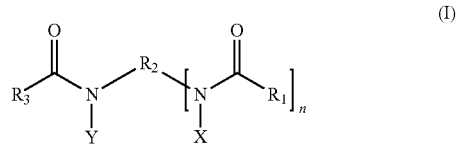

in which:
 $R_1$ and $R_3$ denote, independently of one another, an alkyl radical containing from 1 to 25 carbon atoms;
 $R_2$ denotes a spacer consisting of a linear or branched alkylene chain containing from 1 to 12 carbon atoms;
 X and Y denote, independently of one another, a $-(C_2H_4O)_a-(C_3H_6O)_b Z$ group where
  Z denotes a hydrogen atom or a radical $-CH_2-COOM$, $-SO_3M$, $-P(O)(OM)_2$, $-C_2H_4-SO_3M$, $-C_3H_6-SO_3M$ or $-CH_2(CHOH)_4 CH_2OH$, where M, M' represent H or an alkali metal ion, an alkaline earth metal ion, an ammonium ion or alkanolammonium ion,
  a ranges from 0 to 15,
  b ranges from 0 to 10, and
  the sum of a+b ranges from 1 to 25; and
 n ranges from 1 to 10,
in combination with an effective amount of at least one semi-crystalline polymer which is solid at ambient temperature and which has a melting point of below 70° C., comprising a) a polymeric backbone and b) at least one crystallizable organic side chain and/or one crystallizable organic block which is part of the backbone of said polymer, said polymer having a number-average molecular mass greater than or equal to 2000,
said emulsion having a proportion of fatty phase greater than 10% by weight relative to the total weight of said composition and comprising more than 40% by weight of non-volatile oil(s) relative to the total weight of said fatty phase.

The combination according to the disclosure makes it possible to obtain emulsions which are very homogeneous, which have increased stability and which are therefore compatible with the formulation of materials known to naturally have a destabilizing effect with respect to the known conventional emulsions, and in particular organic UV screens.

In addition, the emulsions stabilized by the combination in accordance with the disclosure have a texture which is very pleasant to the touch. They are soft and give a feeling of lightness when they are applied to the skin.

The term "physiologically acceptable medium" is understood to mean a medium compatible with human keratin materials, such as the skin, the mucus membranes, the nails, the scalp and/or the hair.

Thus, the physiologically acceptable medium is in particular a cosmetically or dermatologically acceptable medium, i.e. with no unpleasant odour, colour or appearance, and which does not generate any tingling, tautness or redness unacceptable to the user.

The composition used according to the disclosure may be intended for cosmetic or pharmaceutical use, particularly dermatological use. Preferably, the composition according to the disclosure is intended for cosmetic use. It may be used for caring for or making up keratin materials.

A composition according to the disclosure is in particular suitable for topical application to a keratin material, and in particular the skin.

Thus, it may be used as a skincare product, for example as a protection, treatment or care cream for the face, for the hands or for the body, such as a body milk for protecting or caring for the skin, the scalp or the mucus membranes, or as a hygiene product, for example as a makeup-removing product for the skin or the mucus membranes, or else as a hair product, or more particularly as a suntan product.

The compositions according to the disclosure may also constitute products for making up the skin and/or the hair, for example by incorporating therein pigments in order to constitute in particular foundations.

Thus, a subject of the disclosure is also the cosmetic use of the composition as defined above, as a skincare product, as a hygiene product, as a hair product, as a suntan product or as a makeup product.

The disclosure futures relates to a cosmetic method for making up and/or for the non therapeutic care of keratin materials, such as skin, scalp, hair, eyelashes, eyebrows, nails and mucous membranes, wherein it comprises at least a step of applying to keratin materials a composition according to the present disclosure.

Another subject of the disclosure is a process for the treatment, in particular cosmetic treatment, of a keratin material, such as the skin, scalp, hair, eyelashes, eyebrows, nails or mucus membranes, characterized in that a composition as defined above is applied to the keratin material.

Other subjects, characteristics, aspects and advantages of the present disclosure will emerge more clearly on reading the description and the examples which follow.

Gemini Surfactant

The gemini surfactant of formula (I) is preferably such that each of the groups $R_1$—CO— and $R_3$—CO— contains from 8 to 20 carbon atoms, and preferably denotes a coconut fatty acid residue (predominantly comprising lauric acid and myristic acid).

In addition, this surfactant is preferably such that, for each of the radicals X and Y, the sum of a and b has a mean value ranging from 10 to 20 and is preferably equal to 15. A preferred group for Z is the group —$SO_3M$ where M is preferably an alkali metal ion such as a sodium ion.

The spacer $R_2$ advantageously consists of a linear $C_1$-$C_3$ alkylene chain, and preferably an ethylene chain ($CH_2CH_2$).

Finally, n is advantageously equal to 1.

A surfactant of this type is in particular the surfactant identified by the INCI name: Sodium dicocoylethylenediamine PEG-15 sulfate, having the following structure:

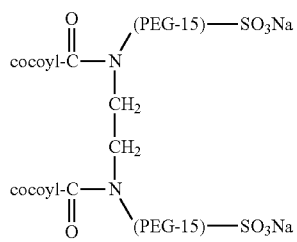

it being understood that PEG represents the group $CH_2CH_2O$, and cocoyl represents the coconut fatty acid residue.

This surfactant has a molecular structure very similar to that of ceramide-3.

Preferably, the gemini surfactant according to the disclosure is used as a mixture with other surfactants, and in particular as a mixture with (a) a glyceryl ester of a $C_6$-$C_{22}$ fatty acid preferably of $C_{14}$-$C_{20}$ such as a stearate), (b) a glycerol diester of a $C_6$-$C_{22}$ fatty acid (preferably of $C_{14}$-$C_{20}$ such as a stearate) and of citric acid (such as a glycerol diester of a $C_6$-$C_{22}$ fatty acid and of monocitric acid), and (c) a $C_{10}$-$C_{30}$ fatty alcohol (preferably behenyl alcohol).

Advantageously, the composition according to the disclosure comprises a mixture of sodium dicocoylethylenediamine PEG-15 sulfate, of glyceryl stearate, of glyceryl stearate monocitrate, of behenyl alcohol.

More preferentially, the gemini surfactant according to the disclosure represents from 10% to 20% by weight, and advantageously 15% by weight; the glyceryl ester of a $C_6$-$C_{22}$ fatty acid represents from 30% to 40% by weight, advantageously 35% by weight; the glycerol diester of a $C_6$-$C_{22}$ fatty acid and of citric acid represents from 10% to 20% by weight, advantageously 15% by weight; and the $C_{10}$-$C_{30}$ fatty alcohol represents from 30% to 40% by weight, advantageously 35% by weight, relative to the total weight of the mixture of surfactants containing the gemini surfactant.

Advantageously, the composition according to the disclosure comprises a mixture of 10 to 20% by weight of sodium dicocoylethylenediamine PEG-15 sulfate, of 30 to 40% (in particular 35%) by weight of glyceryl stearate, of 10 to 20% (in particular 15%) by weight of glyceryl stearate monocitrate, of 30 to 40% (in particular 35%) by weight of behenyl alcohol, relative to the total weight of surfactants containing the gemini surfactant.

As a variant, the gemini surfactant according to the disclosure may be used as a mixture with an anionic surfactant such as a lauric acid ester, sodium lauryl lactate. In this case, the gemini surfactant preferably represents from 30% to 50% by weight, and the anionic surfactant represents from 50% to 70% by weight, relative to the total weight of the mixture.

The gemini surfactant may be used, for example, as a mixture with other surfactants in the form of products sold by the company Sasol under the name Ceralution®, and in particular the following products:

Ceralution® H: Behenyl Alcohol, Glyceryl Stearate, Glyceryl Stearate Citrate and Sodium Dicocoylethylenediamine PEG-15 Sulfate, Ceralution® F: Sodium Lauroyl Lactylate and Sodium Dicocoylethylenediamine PEG-15 Sulphate, Ceralution® C: Aqua, Capric/Caprylic triglyceride, Glycerin, Ceteareth-25, Sodium Dicocoylethylenediamine PEG-15 Sulfate, Sodium Lauroyl Lactylate, Behenyl Alcohol, Glyceryl Stearate, Glyceryl Stearate Citrate, Gum Arabic, Xanthan Gum, Phenoxyethanol, Methyl paraben, Ethyl paraben, Butyl paraben, Isobutyl paraben (INCI names).

This gemini surfactant represents from 3% to 50% of the weight of these mixtures.

The gemini surfactant of formula (I) may be present in a composition according to the disclosure at a content ranging from 0.01% to 5% by weight, relative to the total weight of the composition, preferably ranging from 0.1% to 3% by weight, and better still ranging from 0.2% to 1.5% by weight.

Semi-crystalline Polymer

The semi-crystalline polymer used in the composition of the disclosure is generally introduced into the liquid fatty phase of the emulsion.

For the purpose of the disclosure, the term "semi-crystalline polymer" is intended to mean polymers comprising a crystallizable portion, pendant chain or block in the backbone, and an amorphous portion in the backbone, and having a first-order reversible phase change temperature, in particular melting temperature (solid-liquid transition). For the purpose of the disclosure, the term "polymers" is intended to mean compounds comprising at least 2 repeating units, preferably at least 3 repeating units, and more especially at least 10 repeating units. When the crystallizable portion is a block of the polymer backbone, the chemical nature of this crystallizable block is different from that of the amorphous blocks; the semi-crystalline polymer is, in this case, a block polymer, for example of the diblock, triblock or multiblock type.

Advantageously, the semi-crystalline polymer(s) of the composition of the disclosure has (have) a number-average molecular mass $\overline{M}n$ of greater than or equal to 2000, ranging, for example, from 2000 to 800 000, preferably from 3000 to 500 000, for example from 4000 to 150 000, and better still from 4000 to 99 000.

In the composition according to the disclosure, the semi-crystalline polymers are advantageously soluble in the fatty phase to at least 1% by weight, at a temperature above their melting point. Outside the crystallizabled chains or blocks, the blocks of the polymers are amorphous. For the purpose of the disclosure, the term "crystallizable chain or block" is intended to mean a chain or block which, if it was alone, would pass from the amorphous state to the crystalline state, reversibly, depending on whether the temperature is above or below the melting point. For the purpose of the disclosure, a chain is a group of atoms that is pendant or lateral relative to the backbone of the polymer. A block is a group of atoms belonging to the backbone, this group constituting one of the repeating units of the polymer.

Preferably, the polymer backbone of the semi-crystalline polymers is soluble in the liquid fatty phase.

Preferably, the semi-crystalline polymers used in the composition of the disclosure have a melting point (or melting temperature) Tm of less than 70° C., preferably less than 50° C., this temperature being at least equal to the temperature of the keratin support that is to receive the composition according to the disclosure. The semi-crystalline polymer has a melting point Tm such that 25° C.≤Tm<70° C., and preferably 30° C.≤Tm<50° C. The melting point can be measured especially by any known method, and in particular using a differential scanning calorimeter (DSC).

Preferably, the crystallizable blocks or chains of the semi-crystalline polymers represent at least 30% of the total weight of each polymer, and better still at least 40%. The semi-crystalline polymers of the disclosure comprising crystallizable blocks are block or multiblock polymers. They can be obtained by polymerization of monomers containing reactive doubles bonds (ethylenic bonds) or by a polycondensation. When the polymers of the disclosure are polymers comprising crystallizable side chains, said polymers are advantageously in random form.

Preferably, the semi-crystalline polymers of the disclosure are of synthetic origin. In addition, they do not comprise a polysaccharide backbone.

The semi-crystalline polymers that can be used in the disclosure are in particular:

1) block copolymers of polyolefins of controlled crystallization, the monomers of which are described in document EP-A-951897;

2) polycondensates and especially aliphatic or aromatic polyester polycondensates, and aliphatic/aromatic copolyesters;

3) homopolymers or copolymers bearing at least one crystallizable side chain, and homopolymers or copolymers bearing in the backbone at least one crystallizable block, for instance those described in document U.S. Pat. No. 5,156,911;

4) homopolymers or copolymers bearing at least one crystallizable side chain comprising one (or more) fluoro group(s), as described in document WO-A-01/19333;

5) and mixtures thereof.

In the last two cases (3 and 4), the crystallizable block(s) or side chain(s) is (are) hydrophobic.

Crystalline polymers comprising crystallizable side chains or bearing in the backbone at least one crystallizable block are described below.

A) Semi-crystalline Polymers Comprising Crystallizable Side Chains

Mention may in particular be made of those defined in documents U.S. Pat. No. 5,156,911 and WO-A-01/19333. They are homopolymers or copolymers comprising from 50% to 100% by weight of units resulting from the polymerization of one or more monomers bearing crystallizable hydrophobic side chain(s).

These homopolymers or copolymers are of any nature provided that they meet the conditions indicated hereinafter with, in particular, the characteristic of being soluble or dispersible in the liquid fatty phase by heating above their melting point Tm. They may result:

from the polymerization, especially free-radical polymerization, of one or more monomers comprising reactive ethylenic double bond(s) with respect to a polymerization, i.e. comprising a vinyl, (meth)acrylic or allylic group;

from the polycondensation of one or more monomers bearing coreactive groups (carboxylic acid, sulphonic acid, alcohol, amine or isocyanate), such as, for example, polyesters, polyurethanes, polyethers, polyureas or polyamides.

a) In general, the crystallizable units (chains or blocks) of the semi-crystalline polymers according to the disclosure are obtained from monomer(s) comprising crystallizable block(s) or chain(s), used for the production of the semi-crystalline polymers. These polymers are chosen in particular from homopolymers and copolymers resulting from the polymerization of at least one monomer comprising a crystallizable chain or chains which may be represented by the formula X:

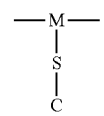

where M represents an atom of the polymer skeleton, S represents a spacer and C represents a crystallizable group.

The crystallizable chains "—S—C" may be aliphatic or aromatic, and optionally fluorinated or perfluorinated. "S" in particular represents a linear or branched or cyclic group $(CH_2)_n$ or $(CH_2CH_2O)_n$ or $(CH_2O)$, n being an integer ranging from 0 to 22. Preferably, "S" is a linear group. Preferably, "S" and "C" are different.

When the crystallizable chains are aliphatic (alkyl) chains, they comprise at least 11 carbon atoms and not more than 40 carbon atoms and better still not more than 24 carbon atoms. They are in particular alkyl chains containing at least 12 carbon atoms, and are preferably alkyl chains containing from 14 to 24 carbon atoms ($C_{14}$-$C_{24}$). They may be hydrocarbon-based alkyl chains (carbon and hydrogen atoms) or fluoroalkyl or perfluoroalkyl chains (carbon atoms, fluorine atoms and, optionally, hydrogen atoms). When they are fluoroalkyl or perfluoroalkyl chains, they comprise at least 11 carbon atoms, at least 6 carbon atoms of which are fluorinated.

As examples of semi-crystalline polymers or copolymers comprising crystallizable chain(s), mention may be made of those resulting from the polymerization of at least one monomer comprising a crystallizable chain chosen from saturated $C_{14}$-$C_{24}$ alkyl(meth)acrylates ($C_{14}$-$C_{24}$ means that the alkyl group contains from 14 to 24 carbon atoms); $C_{11}$-$C_{15}$ perfluoroalkyl(meth)acrylates (alkyl group with 11 to 15 carbon atoms); $C_{14}$ to $C_{24}$ N-alkyl(meth)acrylamides with or without a fluorine atom (alkyl group with 14 to 24 carbon atoms); vinyl esters comprising $C_{14}$ to $C_{24}$ alkyl or perfluoroalkyl chains (alkyl group with 14 to 24 carbon atoms), with a perfluoroalkyl chain containing at least 6 fluorine atoms; vinyl ethers comprising $C_{14}$ to $C_{24}$ alkyl or perfluoroalkyl chains (alkyl group with 14 to 24 carbon atoms), with a perfluoroalkyl chain containing at least 6 fluorine atoms; $C_{14}$ to $C_{24}$ alpha-olefins (alkyl group with 14 to 24 carbon atoms), such as, for example, octadecene; $C_{14}$ to $C_{24}$ para-alkylstyrenes (alkyl group with 14 to 24 carbon atoms), and mixtures thereof.

For the purpose of the disclosure, the term "alkyl" is intended to mean a saturated group in particular containing from 8 to 24 carbon atoms ($C_8$ to $C_{24}$), unless otherwise mentioned.

When the polymers result from a polycondensation, the hydrocarbon-based and/or fluorinated crystallizable chains as defined above are borne by a monomer which may be a diacid, a diol, a diamine or a diisocyanate.

When the polymers used in the composition of the disclosure are copolymers, they also contain from 0 to 50% of groups Y or Z resulting from the copolymerization:

α) with Y which is a polar or nonpolar monomer or a mixture of the two:
when Y is a polar monomer, it is either a monomer bearing polyoxyalkylenated (in particular oxyethylenated and/or oxypropylenated) groups, a hydroxyalkyl(meth)acrylate such as hydroxyethyl acrylate, (meth)acrylamide, an N-alkyl(meth)acrylamide, an N,N-dialkyl(meth)acrylamide such as, for example, N,N-diisopropylacrylamide or N-vinylpyrrolidone (NVP), N-vinylcaprolactam, or a monomer bearing at least one carboxylic acid group, for instance (meth)acrylic acid, crotonic acid, itaconic acid, maleic acid or fumaric acid or bearing a carboxylic acid anhydride group, for instance maleic anhydride, and mixtures thereof.
When Y is a nonpolar monomer, it may be an ester of the linear, branched or cyclic alkyl(meth)acrylate type, a vinyl ester, an alkyl vinyl ether, an alpha-olefin, styrene or styrene substituted with an alkyl group containing from 1 to 10 carbon atoms ($C_1$ to $C_{10}$), for instance α-methylstyrene, or a macromonomer of the polyorganosiloxane type containing vinylic unsaturation;

β) with Z which is a polar monomer or a mixture of polar monomers, Z having the same definition as the "polar Y" defined above.

Preferably, the semi-crystalline polymers comprising a crystallizable side chain are chosen from alkyl(meth)acrylate or alkyl(meth)acrylamide homopolymers with an alkyl group as defined above, and in particular of $C_{14}$-$C_{24}$; the copolymers of these monomers with a hydrophilic monomer preferably different in nature from (meth)acrylic acid; and mixtures thereof. They may be, for example, as copolymers, copolymers of alkyl (meth)acrylate or of alkyl(meth)acrylamide with a $C_{14}$ to $C_{24}$ alkyl group, with N-vinylpyrrolidone, hydroxyethyl(meth)acrylate; or mixtures thereof.

B) Polymers Bearing in the Backbone at Least One Crystallizable Block

These are again polymers that are soluble or dispersible in the liquid fatty phase by heating above their melting point Tm. These polymers are in particular block copolymers consisting of at least 2 blocks of different chemical nature, one of which is crystallizable.

The following may be used:
1) the polymers defined in document U.S. Pat. No. 5,156,911;
2) block copolymers of olefin or of cycloolefin comprising a crystallizable chain, such as those derived from block polymerization of:
cyclobutene, cyclohexene, cyclooctene, norbornene (i.e. bicyclo(2,2,1)hept-2-ene), 5-methylnorbornene, 5-ethylnorbornene, 5,6-dimethylnorbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a,5,8a-octahydronaphthalene, dicyclopentadiene, or mixtures thereof;
with ethylene, propylene, 1-butene, 3-methyl-1-butene, 1-hexene, 4-methyl-1-pentene, 1-octene, 1-decène or 1-eicosene, or mixtures thereof.

These block copolymers may in particular be (ethylene/norbornene) block copolymers and (ethylene/propylene/ethylidenenorbornene) block terpolymers.

Those resulting from the block copolymerization of at least 2 $C_2$-$C_{16}$ and better still $C_2$-$C_{12}$ α-olefins, such as those mentioned above and in particular block bipolymers of ethylene and of 1-octene, may also be used.

3) Copolymers containing at least one crystallizable block, the rest of the copolymer being amorphous (at room temperature). These copolymers may also have two crystallizable blocks of different chemical nature. The preferred copolymers are those simultaneously containing at room temperature a crystallizable block and an amorphous block that is both hydrophobic and lipophilic sequentially distributed; mention may, for example, be made of polymers containing one of the crystallizable blocks below and one of the amorphous blocks below:

Naturally crystallizable block: a) polyester, for instance poly(alkylene terephthalate), b) polyolefin, for instance polyethylenes or polypropylenes.

Amorphous or lipophilic block, for instance amorphous polyolefins or amorphous copoly(olefins) such as poly (isobutylene), hydrogenated polybutadiene or hydrogenated poly(isoprene).

As examples of such copolymers comprising a crystallizable block and an amorphous block, mention may be made of:

α) poly(ε-caprolactone)-b-poly(butadiene) block copolymers, preferably used in hydrogenated form, such as those described in the article "Melting behavior of poly(ε-caprolactone)-block-polybutadiene copolymers" by S. Nojima, Macromolecules, 32, 3727-3734 (1999).

β) Block or multiblock hydrogenated poly(butylene terephthalate)-b-poly(isoprene) block copolymers, mentioned in the article "Study of morphological and mechanical properties of PP/PBT" by B. Boutevin et al., Polymer Bulletin, 34, 117-123 (1995).

γ) The poly(ethylene)-b-copoly(ethylene/propylene) block copolymers mentioned in the articles "Morphology of semi-crystalline block copolymers of ethylene-(ethylene-alt-propylene)" by P. Rangarajan et al., Macromolecules, 26, 4640-4645 (1993), and "Polymer aggregates with crystalline cores: the system poly(ethylene)-poly(ethylene-propylene)" P. Richter et al., Macromolecules, 30, 1053-1068 (1997).

δ) The poly(ethylene)-b-poly(ethylethylene) block copolymers mentioned in the general article "Crystallization in block copolymers" by I. W. Hamley, Advances in Polymer Science, Vol. 148, 113-137 (1999).

The semi-crystalline polymers of the composition of the disclosure may be non-crosslinked or partially crosslinked, provided that the degree of crosslinking does not harm their dissolution or dispersion in the liquid fatty phase by heating above their melting point. This may then be a chemical crosslinking, by reaction with a multifunctional monomer during the polymerization. It may also be physical crosslinking which may then be due either to the establishment of bonds of hydrogen type or dipolar type between groups borne by the polymer, such as, for example, the dipolar interactions between carboxylate ionomers, these interactions being of small amount and borne by the polymer backbone; or to a phase separation between the crystallizable blocks and the amorphous blocks borne by the polymer.

Preferably, the semi-crystalline polymers of the composition according to the disclosure are non-crosslinked.

By way of specific example of a semi-crystalline polymer that can be used in the composition according to the disclosure, mention may be made of the Intelimer® products from the company Landec described in the brochure "Intelimer® polymers". These polymers are in solid form at ambient temperature (25° C.). They bear crystallizable side chains and have the monomer of above formula X. Mention may in particular be made of "Landec IP22", having a melting point Tm of 56° C., which is an impermeable, non-sticky product that is viscous at ambient temperature.

The semi-crystalline polymers described in Examples 3, 4, 5, 7 and 9 of document U.S. Pat. No. 5,156,911, resulting from the copolymerization of acrylic acid and of a $C_5$ to $C_{16}$ alkyl(meth)acrylate having a Tm ranging from 20° C. to 35° C. may also be used, and more particularly those resulting from the copolymerization:
of acrylic acid, of hexadecyl acrylate and of isodecyl acrylate in a 1/16/3 ratio,
of acrylic acid and of pentadecyl acrylate in a 1/19 ratio,
of acrylic acid, of hexadecyl acrylate and of ethyl acrylate in a 2.5/76.5/20 ratio,
of acrylic acid, of hexadecyl acrylate and of methyl acrylate in a 5/85/10 ratio,
of acrylic acid and of octadecyl methacrylate in a 2.5/97.5 ratio.

The polymer "Structure O" sold by the company National Starch, such as the product described in document U.S. Pat. No. 5,736,125, with a Tm of 44° C., and also semi-crystalline polymers comprising crystallizable pendant chains comprising fluorinated groups, as described in examples 1, 4, 6, 7 and 8 of document WO-A-01/19333, may also be used.

The semi-crystalline polymers obtained by copolymerization of stearyl acrylate and of acrylic acid or of NVP, as described in document U.S. Pat. No. 5,519,063 or EP-A-0550745, and more especially those described in the polymer Preparation Examples 1 and 2 below, with a melting point of 40° C. and 38° C., respectively, may also be used.

The semi-crystalline polymers obtained by copolymerization of behenyl acrylate and of acrylic acid or of NVP, as described in documents U.S. Pat. No. 5,519,063 and EP-A-0 550 745, and more especially those described in the polymer Preparation Examples 3 and 4 below, with a melting point of 60° C. and 58° C., respectively, may also be used.

According to a specific embodiment of the disclosure, the semi-crystalline polymers used do not comprise a carboxylic group.

The amount of semi-crystalline polymer in the composition of the disclosure may range, for example, from 0.1% to 30% by weight of active material, preferably from 0.5% to 20% by weight of active material, and better still from 1% to 10% by weight of active material, and preferably from 1% to 5% by weight, relative to the total weight of the composition.

In particular, the semi-crystalline polymer and the gemini surfactant may be present in a composition according to the disclosure in a semi-crystalline polymer(s)/gemini surfactant(s) weight ratio ranging from 1 to 10, in particular ranging from 1.5 to 9.

Fatty Phase

As previously specified, the composition is an oil-in-water emulsion, the fatty phase of which may range from 10% to 50% by weight, in particular from 15% to 45% by weight, and preferably from 20% to 40% by weight, relative to the total weight of the composition.

For the purpose of the disclosure, the fatty phase includes any liquid fatty substances, generally oils, or solid fatty substances like waxes, or pasty compounds present in said composition.

This fatty phase contains at least 40% by weight of non-volatile oil(s) as described below.

The term "oil" is intended to mean any fatty substance in liquid form at ambient temperature (25° C.) and at atmospheric pressure.

The oil(s) may be present in a proportion of from 0.1% to 50% by weight, in particular of at least 5% to 40% by weight, relative to the total weight of the cosmetic composition according to the disclosure.

The volatile or non-volatile oils may be hydrocarbon-based oils of animal or plant origin, synthetic oils, silicone oils, fluoro oils, or mixtures thereof.

For the purpose of the present disclosure, the term "silicone oil" is intended to mean an oil comprising at least one silicon atom, and in particular at least one Si—O group.

The term "hydrocarbon-based oil" is intended to mean an oil containing principally hydrogen and carbon atoms and, optionally, oxygen, nitrogen, sulphur and/or phosphorus atoms.

Non-volatile Oils

For the purpose of the present disclosure, the term "non-volatile oil" is intended to mean an oil having a vapour pressure of less than 0.13 Pa (0.01 mmHg).

The non-volatile oils may in particular be chosen from non-volatile hydrocarbon-based, where appropriate fluorinated, oils and/or non-volatile silicone oils.

As non-volatile hydrocarbon-based oils that are suitable for use in the disclosure, mention may be made especially of:
hydrocarbon-based oils of animal origin,
hydrocarbon-based oils of plant origin such as phytostearyl esters, such as phytostearyl oleate, phytostearyl isostearate and lauroyl/octyldodecyl/phytostearyl glutamate, for example sold under the name Eldew PS203 by Ajinomoto, triglycerides consisting of fatty acid esters of glycerol, the fatty acids of which may have chain lengths ranging from $C_4$ to $C_{24}$, these chains possibly being linear or branched, and saturated or unsaturated; these oils are especially heptanoic or octanoic triglycerides, wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cotton seed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion flower oil or musk rose oil; shea butter; or alternatively caprylic/capric acid triglycerides, for instance those sold by the company Stearineries Dubois or those sold under the names Miglyol 810®, 812® and 818® by the company Dynamit Nobel, hydrocarbon-based oils of mineral or synthetic origin, for instance:
  synthetic ethers containing from 10 to 40 carbon atoms;
  linear or branched hydrocarbons of mineral or synthetic origin such as petroleum jelly, polydecenes, hydrogenated polyisobutene such as Parleam, and squalane, and mixtures thereof and in particular hydrogenated polyisobutene,
    synthetic esters, for instance oils of formula $R_1COOR_2$ in which $R_1$ represents a linear or branched fatty acid residue containing from 1 to 40 carbon atoms and $R_2$ represents a hydrocarbon-based chain that is especially branched, containing from 1 to 40 carbon atoms provided that $R_1+R_2 \geq 10$.

The esters may be chosen especially from fatty acid esters, for example:
  cetostearyl octanoate, isopropyl alcohol esters, such as isopropyl myristate or isopropyl palmitate, ethyl palmitate, 2-ethylhexyl palmitate, isopropyl stearate or isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate and palmitate, alkyl benzoate, polyethylene glycol diheptanoate, propylene glycol 2-diethylhexanoate, and mixtures thereof, $C_{12}$ to $C_{15}$ alcohol benzoates, hexyl laurate, neopentanoic acid esters, for instance isodecyl neopentanoate, isotridecyl neopentanoate, isostearyl neopentanoate and octyldodecyl neopentanoate, isononanoic acid esters, for instance isononyl isononanoate, isotridecyl isononanoate and octyl isononanoate, and hydroxylated esters, for instance isostearyl lactate and diisostearyl malate;
  polyol esters and pentaerythritol esters, for instance dipentaerythritol tetrahydroxystearate/tetraisostearate;
  esters of diol dimers and diacid dimers such as Lusplan DD-DA5® and Lusplan DD-DA7®, sold by the company Nippon Fine Chemical and described in application FR 03 02809,
  fatty alcohols that are liquid at ambient temperature, with a branched and/or unsaturated carbon-based chain containing from 12 to 26 carbon atoms, for instance 2-octyldodecanol, isostearyl alcohol, oleyl alcohol, 2-hexyldecanol, 2-butyloctanol and 2-undecylpentadecanol;
  higher fatty acids such as oleic acid, linoleic acid or linolenic acid, and mixtures thereof, and
  dialkyl carbonates, the 2 alkyl chains possibly being identical or different, such as dicaprylyl carbonate sold under the name Cetiol CC® by Cognis,
  non-volatile silicone oils, for instance non-volatile polydimethylsiloxanes (PDMSs), polydimethylsiloxanes comprising alkyl or alkoxy groups that are pendant and/or at the end of a silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and dimethicones or phenyl trimethicones with a viscosity of less than or equal to 100 cSt, and mixtures thereof,
  and mixtures thereof.

The non-volatile oils may also be chosen from liquid organic screens such as those mentioned hereinafter among the list of organic UV screens.

The non-volatile oils may be present in a composition according to the disclosure at a content ranging from 1% to 40% by weight, in particular from 3% to 20% by weight, relative to the total weight of the composition.

Volatile Oils

A composition in accordance with the disclosure may also comprise at least one volatile oil.

For the purpose of the present disclosure, the term "volatile oil" is intended to mean an oil (or nonaqueous medium) capable of evaporating on contact with the skin in less than one hour, at ambient temperature and at atmospheric pressure. The volatile oil is a volatile cosmetic oil, which is liquid at ambient temperature, especially having a non-zero vapour pressure, at ambient temperature and atmospheric pressure, in particular having a vapour pressure ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The volatile hydrocarbon-based oils may be chosen from hydrocarbon-based oils containing from 8 to 16 carbon atoms, and in particular branched $C_8$-$C_{16}$ alkanes (also known as isoparaffins), such as isododecane (also known as 2,2,4,4,6-pentamethylheptane), isodecane, isohexadecane and, for example, the oils sold under the trade names Isopar® or Permethyl®.

Volatile oils that may also be used include volatile silicones, for instance volatile linear or cyclic silicone oils, especially those having a viscosity ≤8 centistokes ($8\times10^{-6}$ m²/s), and especially containing from 2 to 10 silicon atoms, and in particular from 2 to 7 silicon atoms, these silicones optionally comprising alkyl or alkoxy groups containing from 1 to 10 carbon atoms. As a volatile silicone oil that can be used in the disclosure, mention may in particular be made of dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Volatile fluoro oils such as nonafluoromethoxybutane or perfluoromethylcyclopentane, and mixtures thereof, may also be used.

It is also possible to use a mixture of the oils mentioned above.

According to a variant embodiment, the compositions according to the disclosure contain at least 5% by weight, or even at least 10% by weight, of non-silicone oil(s).

The other fatty substances that may be present in the oily phase are, for example, fatty acids containing from 8 to 30 carbon atoms, such as stearic acid, lauric acid or palmitic acid; fatty alcohols containing from 8 to 30 carbon atoms, such as stearyl alcohol, cetyl alcohol and mixtures thereof (cetearyl alcohol).

The liquid fatty phase may also contain, in addition to the oils, other compounds solubilized in the oils, such as gelling and/or structuring agents.

These compounds may in particular be chosen from gums such as silicone gums (dimethiconol); silicone resins such as trifluoromethyl($C_1$-$C_4$)alkyl dimethicone and trifluoropropyl dimethicone, and silicone elastomers such as the products sold under the name "KSG" by the company Shin-Etsu, under the name "Trefil" by the company Dow Corning or under the name "Gransil" by the company Grant Industries; and mixtures thereof.

Solid Fatty Substances

The composition according to the disclosure may also comprise at least one solid fatty substance chosen from waxes, pasty fatty substances and mixtures thereof.

The wax is solid at ambient temperature (25° C.), with a reversible solid/liquid change of state, having a melting point of greater than 30° C., which may be up to 200° C., and a hardness of greater than 0.5 MPa and having, in the solid state, an anisotropic crystal organization.

It may be a hydrocarbon-based wax, a fluoro wax and/or a silicone wax and may be of animal, plant, mineral or synthetic origin.

It may be chosen, for example, from beeswax, carnauba wax, candelilla wax, paraffin waxes, hydrogenated castor oil, synthetic waxes, for instance polyethylene waxes (preferably with a molecular weight of between 400 and 600) or Fischer-Tropsch waxes, silicone waxes, for instance alkyl or alkoxy dimethicones containing from 16 to 45 carbon atoms, ceresins or ozokerites, for example isoparaffins with a melting point of less than 40° C., such as EMW-0003, sold by the company Nippon Seirou, α-olefin oligomers, such as the polymers Performa V® 825, 103 and 260, sold by the company New Phase Technologies; ethylene-propylene copolymers, such as Performalene® EP 700, and microcrystalline waxes with a melting point greater than 85° C., such as HI-MIC® 1070, 1080, 1090 and 3080, sold by Nippon Seirou, and mixtures thereof.

According to a specific embodiment, the wax(es) used in the cosmetic compositions in accordance with the present disclosure may be present at a content ranging from approximately 1% or approximately 20%, in particular from approximately 2% to approximately 10%, relative to the total weight of the composition.

A cosmetic composition in accordance with the present disclosure may also comprise at least one pasty compound.

For the purpose of the present disclosure, the term "pasty" is intended to mean a fatty compound with a reversible solid/liquid change of state, and comprising, at a temperature of 23° C., a liquid fraction and a solid fraction. The term "pasty" also refers to polyvinyl laurate.

For the purposes of the disclosure, a pasty compound may advantageously have a hardness at 20° C. ranging from 0.001 to 0.5 MPa, and preferably from 0.002 to 0.4 MPa.

Among the pasty compounds that may be used in the composition according to the disclosure, mention may be made of petroleum jelly, shea butter, cocoa butter, shorea butter, lanolins and lanolin derivatives such as acetylated lanolins, oxypropylenated lanolins or isopropyl lanolate, and mixtures thereof. Esters of fatty acids or of fatty alcohols may also be used, in particular those containing 20 to 65 carbon atoms, such as triisostearyl citrate or cetyl citrate; arachidyl propionate; polyvinyl laurate; cholesterol esters, for instance triglycerides of plant origin such as hydrogenated plant oils, viscous polyesters and mixtures thereof. Triglycerides of plant origin that may be used include hydrogenated castor oil derivatives, such as Thixinr®' from Rheox.

Mention may also be made of polyesters resulting from the esterification of a carboxylic acid and of an aliphatic hydroxycarboxylic ester. For example, Risocast® DA-L (ester derived from the esterification reaction of hydrogenated castor oil with dilinoleic acid in proportions of 2 to 1) and Risocast® DA-H (ester resulting from the esterification of hydrogenated castor oil with isostearic acid in proportions of 4 to 3) sold by the Japanese company Kokyu Alcohol Kogyo.

Mention may also be made of pasty silicone compounds such as high-molecular-weight polydimethylsiloxanes (PDMSs), and in particular those containing pendant chains of the alkyl or alkoxy type containing from 8 to 24 carbon atoms, and having a melting point of 20-55° C., for instance stearyl dimethicones, especially those sold by the company Dow Corning under the trade names DC2503® and DC25514®, and mixtures thereof.

The composition may also comprise a cosmetic additive in particular chosen from fillers, surfactants, cosmetic or dermatological active agents, UV screens, film-forming polymers, gelling agents, preservatives, fragrances, pigments, active agents such as vitamins, and plant extracts.

As specified above, the compositions according to the disclosure are particularly advantageous for formulating organic screens.

Organic UV Screens (or Sunscreens)

Thus, according to a variant embodiment, the compositions according to the disclosure contain one or more organic screens.

More specifically, the composition of the disclosure may contain at least one organic UV screen chosen from hydrophilic organic screens, lipophilic organic screens and mixtures thereof. According to a specific embodiment of the disclosure, one or more physical screens may be combined therewith.

As examples of organic screens which are active in the UV-A and/or UV-B range, and which may be used in the composition of the disclosure, mention may, for example, be made of the following, denoted below by their CTFA name:

Derivatives of Para-aminobenzoic Acid (PABA):

PABA,

Ethyl PABA,

Ethyl Dihydroxypropyl PABA,

Ethylhexyl Dimethyl PABA sold in particular under the name "Escalol 507" by ISP, Glyceryl PABA (liquid), PEG-25 PABA sold under the name "Uvinul P25" by BASF, Salicylic Derivatives:
Homosalate sold under the name "Eusolex HMS" by Rona/EM Industries (liquid),
Ethylhexyl Salicylate (or ethyl hexyl salicylate) sold under then name "Neo Heliopan OS" by Haarmann and Reimer (liquid),
Dipropylene glycol Salicylate sold under the name "Dipsal" by Scher,
TEA Salicylate, sold under the name "Neo Heliopan TS" by Haarmann and Reimer (liquid),
Dibenzoylmethane Derivatives:
Butyl Methoxydibenzoylmethane sold in particular under the trade name "Parsol 1789" by Hoffmann La Roche (liquid),
Isopropyl Dibenzoylmethane,
Cinnamic Derivatives:
Ethylhexyl Methoxycinnamate (or Octyl Methoxycinnamate) sold in particular under the trade name "Parsol MCX" by Hoffmann La Roche,
Isopropyl Methoxycinnamate,
Isoamyl Methoxycinnamate sold under the trade name "Neo Heliopan E 1000" by Haarmann and Reimer (liquid),
Cinoxate,
DEA Methoxycinnamate (liquid),
Diisopropyl Methylcinnamate (liquid),
Glyceryl Ethylhexanoate Dimethoxycinnamate,
β,β-Diphenlacrylate Derivatives:
Octocrylene (2-ethylhexyl α-cyano-β,β-diphenylacrylate) sold in particular under the trade name "Uvinul N539" by BASF (liquid),
Etocrylene, sold in particular under the trade name "Uvinul N35" by BASF,
Benzophenone Derivatives:
Benzophenone-1 sold under the trade name "Uvinul 400" by BASF,
Benzophenone-2 sold under the trade name "Uvinul D50" by BASF,
Benzophenone-3 or Oxybenzone, sold under the trade name "Uvinul M40" by BASF,
Benzophenone-4 sold under the trade name "Uvinul MS40" by BASF,
Benzophenone-5,
Benzophenone-6 sold under the trade name "Helisorb 11" by Norquay,
Benzophenone-8 sold under the trade name "Spectra-Sorb UV-24" by American Cyanamid,
Benzophenone-9 sold under the trade name "Uvinul DS-49" by BASF,
Benzophenone-12,
Benzylidenecamphor Derivatives:
3-Benzylidene camphor manufactured under the name "Mexoryl SD" by Chimex,
4-Methylbenzylidenecamphor sold under the trade name "Eusolex 6300" by Merck,
Benzylidene Camphor Sulfonic Acid manufactured under the name "Mexoryl SL" by Chimex,
Camphor Benzalkonium Methosulfate manufactured under the name "Mexoryl SO" by Chimex,
Terephthalylidene Dicamphor Sulfonic Acid manufactured under the name "Mexoryl SX" by Chimex,
Polyacrylamidomethyl Benzylidene Camphor manufactured under the name "Mexoryl SW" by Chimex,
Phenylbenzimidazole Derivatives:
Phenylbenzimidazole Sulfonic Acid sold in particular under the trade name "Eusolex 232" by Merck,
Benzimidazilate sold under the trade name "Neo Heliopan AP" by Haarmann and Reimer,
Triazine Derivatives:
Anisotriazine sold under the trade name "Tinosorb S" by Ciba Geigy,
Ethylhexyl triazone sold under the trade name "Uvinul T150" by BASF,
Diethylhexyl Butamido Triazone sold under the trade name "Uvasorb HEB" by Sigma 3V,
Phenylbenzotriazole Derivatives:
Drometrizole Trisiloxane sold under the trade name "Silatrizole" by Rhodia Chimie,
Anthranilic Derivatives:
Menthyl anthranilate sold under the trade name "Neo Heliopan MA" by Haarmann and Reimer (liquid),
Imidazoline Derivatives:
Ethylhexyl Dimethoxybenzylidene Dioxoimidazoline Propionate,
Benzalmalonate Derivatives:
Polyorganosiloxane comprising benzalmalonate functions, sold under the trade name "Parsol SLX" by Hoffmann La Roche,
and mixtures thereof.

The organic UV screens which are more particularly preferred are chosen from the following compounds:
Ethylhexyl salicylate,
Ethylhexyl triazone,
Butyl Methoxydibenzoylmethane,
Ethylhexyl Methoxycinnamate,
Octocrylene,
Phenylbenzimidazole Sulfonic Acid,
Terephthalylidene Dicamphor Sulfonic Acid,
Benzophenone-3,
Benzophenone-4,
Benzophenone-5,
4-Methylbenzylidene camphor,
Benzimidazilate,
Anisotriazine,
Ethylhexyl triazone,
Diethylhexyl Butamido Triazone,
Methylene bis-Benzotriazolyl Tetramethylbutylphenol,
Drometrizole Trisiloxane,
and mixtures thereof.

The organic screen(s) may be present in an amount ranging from 0.1% to 25% by weight, preferably from 1% to 20% by weight, and better still 5% to 15% by weight, relative to the total weight of the composition.

As physical screens that may also be present in the compositions of the disclosure, mentioned may, for example, be made of pigments and nanopigments of metal oxides, which may be coated or uncoated, in particular titanium oxide, iron oxide, zirconium oxide, zinc oxide or cerium oxide, and mixtures thereof, it being possible for these oxides to be in the form of microparticles or nanoparticles (nanopigments), which are optionally coated.

Of course, those skilled in the art will take care to select this or these possible additional compounds, and/or the amount thereof, in such a way that the advantageous properties of the compounds according to the disclosure are not, or are not substantially, impaired by the addition envisaged.

The compounds may be more or less fluid and may have the appearance of a white or coloured cream, an ointment, a milk, a lotion, a mist, a serum, a paste or a mousse.

According to a variant embodiment, they may be in the form of a makeup product such as, for example, a foundation.

They may also advantageously be in the form of suntan products.

The examples which appear hereinafter are given by way of nonlimiting illustration of the field of the disclosure.

The gemini surfactant used in the examples hereinafter is a mixture of Behenyl Alcohol, Glyceryl Stearate, Glyceryl Stearate Citrate and Sodium Dicocoylethylenediamine PEG-15 Sulfate sold by the company Sasoc under the name Ceralution®H.

The semi-crystalline polymer used is a poly(stearyl acrylate) sold by the company Landec under the name Intelimer IPA 13-1.

EXAMPLE 1

A cosmetic composition in accordance with the disclosure and the detailed formulation of which is provided hereinafter in Table I, is prepared and its properties in terms of stability and sensory quality are tested.

Its stability over time is assessed at the end of a period of storage in which said composition is left to stand for 2 months at a temperature of respectively 37° C. then 45° C. By way of comparison, two other formulations were prepared, in which the gemini surfactant is replaced with either a 12/46/42 mixture of cetylstearylglucoside and of cetyl and stearyl alcohols sold by SEPPIC under the name Montanov® (control 1), or polyglyceryl-3 methylglucose distearate sold by Goldschmidt under the name Tegocare 450® (control 2).

The corresponding formulations are also given in Table I below.

Results:

|  | Formula according to the disclosure | Control formula 1 | Control formula 2 |
|---|---|---|---|
| Stability | Satisfactory | Unstable | Unstable |
| Cosmetic properties | Soft, non-greasy, light feel | Heterogeneous, greasy, sticky "soapy" texture (whitening effect) | Heterogeneous, greasy, sticky "soapy" texture (whitening effect) |

In terms of stability, only the emulsion in accordance with the present disclosure is satisfactory. Examination under a microscope makes it possible to observe a fine and regular emulsion, unlike the control formulations, the emulsions of which are coarser and more irregular. These same results are confirmed by macroscopic evaluation. The control formulations exhibit, after two months of storage, whether at 37° C. or at 45° C., a heterogeneous texture with masses visible to the naked eye. Only the formulation according to the disclosure remains smooth and fine.

The combination according to the disclosure manifestly ensures a better dispersion of the silica fillers and effectively prevents agglomeration thereof.

TABLE 1

| Chemical name | Formula according to the disclosure | Control formula 1 | Control formula 2 |
|---|---|---|---|
| Gemini surfactant containing 15% AM Ceralution ® H from the company Sasol | 3.5, i.e. 0.525 AM | — | — |
| Mixture of cetylstearylglucoside and of cetyl and stearyl alcohols (12/46/42) (Montanov 68 ® from SEPPIC) | — | 3.5 | — |
| Mixture of methylglucose monodistearate and of polyglycerol-3 stearate (Tego Care 450 ® from Goldschmidt) | — | — | 2.5 |
| 2-Hexyldecyl laurate | 4 | 4 | 4 |
| Isohexadecane | 8 | 8 | 8 |
| Cyclohexadimethylsiloxane | 2.5 | 2.5 | 2.5 |
| Glycerol | 7 | 7 | 7 |
| 2-Phenyl-5-benzimidazolesulphonic acid | 1.7 | 1.7 | 1.7 |
| 2-Ethylhexyl-p-methoxy-4-cinnamate | 7.5 | 7.5 | 7.5 |
| Poly(stearyl acrylate) (Intelimer IPA 13-1 ® from Landec) | 1 | 1 | 1 |
| Fragrance | 0.5 | 0.5 | 0.5 |
| Preservatives | 0.4 | 0.4 | 0.4 |
| Water | qs 100% | qs 100% | qs 100% |
| Polyacrylamidomethylpropanesulphonic acid partially neutralized with ammonia (Hostacerin AMPS ® from Clariant) | 0.5 | 0.5 | 0.5 |
| Xanthan gum | 0.25 | 0.25 | 0.25 |
| 3,3'-Terephthalylidene-10,10'-dicamphosulphonic acid in water at 33%, not stabilized | 2.12 | 2.12 | 2.12 |
| Sodium hydroxide | qs pH 6.5 | qs pH 6.5 | qs pH 6.5 |
| Silica (SB 700 ® from Miyoshi Kasei) | 3 | 3 | 3 |

EXAMPLE 2

| Moisturizing cream | % |
|---|---|
| Oily phase | |
| Gemini surfactant containing 15% AM (Ceralution ® H from the company Sasol) | 5, i.e. 0.75% AM |
| Hydrogenated isoparaffin (Parleam ® from Nof Corporation) | 10 |
| Polymethylene wax (Cirebelle 303 ® from Sasol) | 4 |
| Mixture of alpha,omega-dihydroxyl polydimethyl-siloxane/polydimethylsiloxane 5 cSt (Dow Corning 1503 fluid ® from Dow Corning) | 7.5 |
| Pentaerithrytyl pentaoctanoate | 5 |
| Hydrogenated polydecene (Silkflo 366 NF Polydecene ® from Ineos) | 5 |
| Poly(stearyl acrylate) (Intelimer IPA 13-1 ® from Landec) | 2 |
| Aqueous phase | |
| Polyacrylamidomethylpropanesulphonic acid partially neutralized with aqueous ammonia and highly crosslinked (Hostacerin AMPS ® from Clariant) | 0.5 |
| Preservatives | qs |
| Glycerol | 7 |
| Water | qs 100% |
| Powder phase | |
| Silica microspheres (SB 700 ® from Miyoshi Kasei) | 3 |

Procedure

After homogenization of the various phases, the oily phase is dispersed in the aqueous phase with stirring at 75° C. A firm cream, which is fondant on application and provides intense nutrition and moisturization without an unpleasant greasy film is obtained. The composition is also stable after storage for 2 months at 25° C. and 37° C.

EXAMPLE 3

Table 2 gives the composition of a formulation in accordance with the disclosure. This table also reports a control formula in which the poly(stearyl acrylate) is replaced with beeswax.

TABLE 2

| Chemical name | Formula according to the disclosure | Control formula |
|---|---|---|
| Gemini surfactant containing 15% AM (Ceralution ® H from the company Sasol) | 3.5, i.e. 0.525 AM | — |
| Cyclohexadimethylsiloxane | 2.5 | 2.5 |
| Glycerol | 7 | 7 |
| 4-tert-Butyl-4'-methoxydibenzoyl-methane | 3 | 3 |
| 2-Ethylhexyl 2-cyano-3,3-diphenylacrylate | 7 | 7 |
| 2-Ethylhexyl salicylate | 5 | 5 |
| Poly(stearyl acrylate) (Intelimer IPA 13-1 ® from Landec) | 2 | — |
| Beeswax | — | 2 |
| Fragrance | 0.1 | 0.1 |
| Preservatives | 0.5 | 0.5 |
| Caprylyl glycol | 0.5 | 0.5 |

TABLE 2-continued

| Chemical name | Formula according to the disclosure | Control formula |
|---|---|---|
| Water | qs 100% | qs 100% |
| Mixture of alpha,omega-dihydroxyl polydimethyl-siloxane/cyclopentadimethylsiloxane (14.7/85.3) (Dow Corning 1501 FL ® from Dow Corning) | 2 | 2 |
| (Polyacrylamidomethylpropanesulphonic acid partially neutralized with ammonia) (Hostacerin AMPS ® from Clariant) | 0.5 | 0.5 |
| Xanthan gum | 0.25 | 0.25 |
| Ethylenediaminetetraacetic acid disodium salt | 0.1 | 0.1 |
| Isononyl isononanoate | 4 | 4 |
| Styrene/acrylate copolymer (Sunspheres Powder ® from Rohm & Haas) | 3 | 3 |

Each composition was conserved for 2 months at temperatures of 25° C., 27° C. and 45° C.

Examination with the naked eye shows that the composition according to the disclosure is homogeneous and smooth, whereas the control composition exhibits masses and is therefore heterogeneous, thereby demonstrating that the presence of poly(stearyl acrylate) makes it possible to obtain a stable composition.

Examination under a microscope after 2 months of storage at 45° C. shows that the composition according to the disclosure is fine, whereas the control composition exhibits zones where the oil droplets have collapsed and therefore a heterogeneity.

Moreover, the composition applied to the skin does not give a greasy feeling, or a shiny effect.

Although the present disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A cosmetic or dermatological composition of oil-in-water type comprising, in a physiologically acceptable medium, at least one gemini surfactant of formula (I):

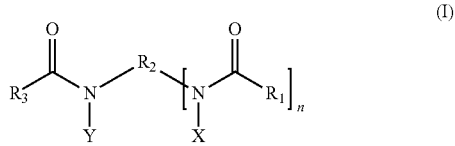

in which:
R$_1$ and R$_3$ denote, independently of one another, an alkyl radical containing from 1 to 25 carbon atoms;
R$_2$ denotes a spacer consisting of a linear or branched alkylene chain containing from 1 to 12 carbon atoms;
X and Y denote, independently of one another, a —(C$_2$H$_4$O)$_a$—(C$_3$H$_6$O)$_b$Z group where:
Z denotes a hydrogen atom or a radical —CH$_2$—COOM, —SO$_3$M, —P(O)(OM)$_2$, —C$_2$H$_4$—SO$_3$M, —C$_3$H$_6$—SO$_3$M, or —CH$_2$(CHOH)$_4$CH$_2$OH, where M, M' represent H or an alkali metal ion, an alkaline earth metal ion, an ammonium ion or alkanolammonium ion, a ranges from 0 to 15, b ranges from 0 to 10, and the sum of a +b ranges from 1 to 25; and n ranges from 1 to 10, in combination with an effective amount of at least one semi-crystalline homopolymer which is solid at ambient temperature and which has a melting point of below 70° C., comprising:

a) a polymeric backbone, and b) at least one crystallizable organic side chain, said homopolymer having a number-average molecular mass greater than or equal to 2000, and said semi-crystalline homopolymer resulting from the polymerization of only monomers comprising a crystallizable chain, selected from the group consisting of C14-C24 alkyl (meth)acrylates, said composition having a proportion of fatty phase greater than 10% by weight relative to a total weight of said composition and comprising more than 40% by weight of non-volatile oil(s) relative to a total weight of the fatty phase, wherein the gemini surfactant is present at a content ranging from 0.01% to 5% by weight, relative to a total weight of the composition.

2. The composition according to claim 1, wherein each of the groups $R_1$—CO— and $R_3$—CO— denotes a coconut fatty acid residue.

3. The composition according to claim 1, wherein, for the gemini surfactant of formula (I), for each of the radicals X and Y, the sum of a and b has a mean value ranging from 10 to 20.

4. The composition according to claim 1, wherein, for the gemini surfactant of formula (I), Y is the group —$SO_3M$ where M is an alkali metal ion.

5. The composition according to claim 1, wherein, for the gemini surfactant of formula (I), n is equal to 1.

6. The composition according to claim 1, wherein the surfactant of formula (I) has the following structure:

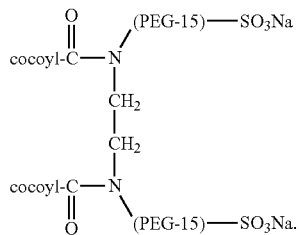

7. The composition according to claim 1, wherein the gemini surfactant is mixed with (a) a glyceryl ester of a $C_6$-$C_{22}$ fatty acid, (b) a glycerol diester of a $C_6$-$C_{22}$ fatty acid and of citric acid, and (c) a $C_{10}$-$C_{30}$ fatty alcohol.

8. The composition according to claim 1, wherein the gemini surfactant is present at a content ranging from 0.2% to 1.5% by weight relative to a total weight of the composition.

9. The composition according to claim 1, wherein the polymer has a number-average molecular mass ranging from 3000 to 500,000.

10. The composition according to claim 1, wherein the polymer is soluble in the fatty phase to at least 1% by weight at a temperature above its melting point.

11. The composition according to claim 1, wherein the polymer has a melting point Tm such that 30° C.≤Tm<50° C.

12. The composition according to claim 1, containing at least one organic UV screen.

13. A cosmetic method for making up and/or for the non therapeutic care of keratin materials, comprising at least a step of applying to keratin materials a composition according to claim 1.

14. The composition according to claim 4, wherein M is a sodium ion.

15. The composition according to claim 1, wherein the gemini surfactant is present at a content ranging from 0.1% to 3% by weight, relative to a total weight of the composition.

* * * * *